United States Patent [19]

Fukunaga et al.

[11] Patent Number: 5,776,047
[45] Date of Patent: Jul. 7, 1998

[54] CARDIOPULMONARY FUNCTION ASSISTING DEVICE

[75] Inventors: Shintaro Fukunaga; Taijiro Sueda; Yuichiro Matsuura, all of Hiroshima, Japan

[73] Assignee: President of Hiroshima University, Hiroshima, Japan

[21] Appl. No.: 515,004

[22] Filed: Aug. 14, 1995

[30] Foreign Application Priority Data

Aug. 19, 1994 [JP] Japan .................. 6-195177

[51] Int. Cl.$^6$ .................................... A61N 1/362
[52] U.S. Cl. ................. 600/18; 604/53; 604/96; 604/101
[58] Field of Search ................. 600/16–18, 53, 600/96, 101, 280; 128/656–58

[56] References Cited

U.S. PATENT DOCUMENTS 4,631,053 12/1986 Taheri .
5,308,319 5/1994 Ide et al. .

FOREIGN PATENT DOCUMENTS 0 422690 4/1991 European Pat. Off. .
0 569318 11/1993 European Pat. Off. .
6-114101 4/1994 Japan .

OTHER PUBLICATIONS

The Japanese Journal of Artificial Organs; vol. 23 Suppln. 1994; Issued on Sep. 15, 1994.

*Primary Examiner*—John P. Lacyk
*Attorney, Agent, or Firm*—Oblon, Spivak, McClelland, Maier & Neustadt, P.C.

[57] ABSTRACT

A cardiopulmonary function assisting device includes a gas guide tube of which peripheral wall does not transmit gas or liquid such as blood and has a suitable rigidity and a suitable flexibility. A header is coaxially attached to an opening at the distal end of the gas guide tube. A plurality of balloons are attached to the distal end of the header. The balloons are formed of a gas permeable film and left in a blood vessel. Oxygen is supplied to the balloons through the gas guide tube, thereby expanding the balloons; oxygen is discharged from the balloons, thereby contracting the balloons. The expanding and contracting operations are repeated. As a result, when the balloons are expanded, oxygen is transmitted through the balloons and added to blood on the periphery of the balloons and the expanded balloons remove the blood away from the periphery. When the balloons are contracted, the periphery of the balloons is filled with blood.

7 Claims, 1 Drawing Sheet

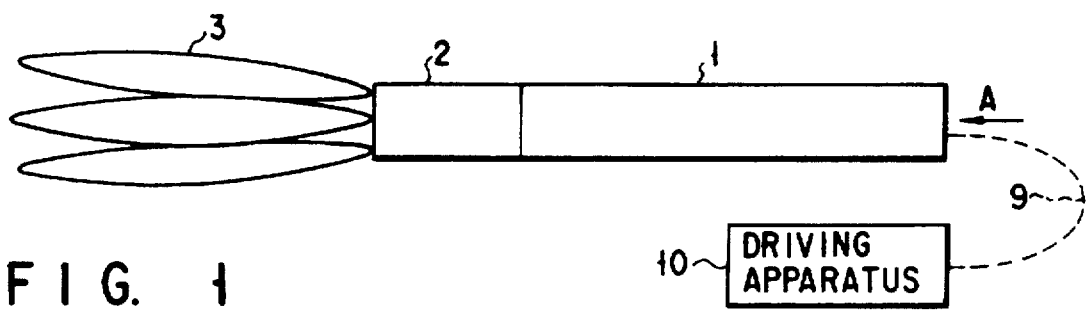
F I G. 1
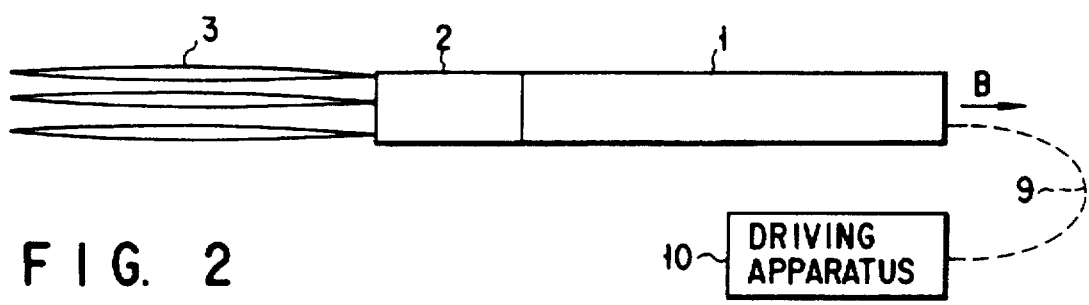
F I G. 2
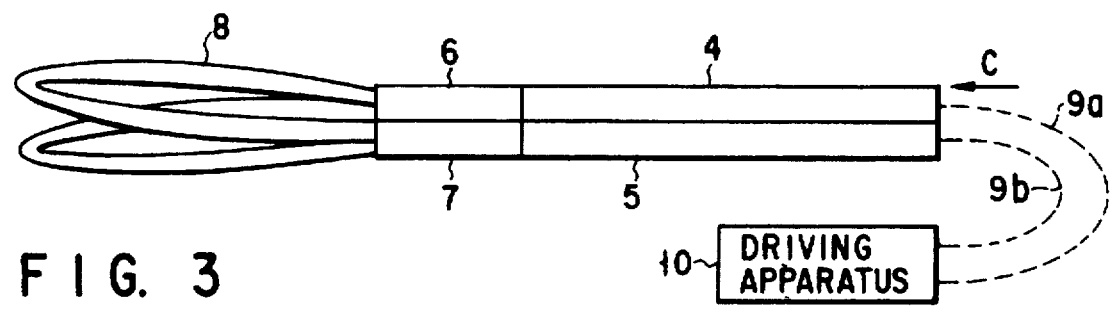
F I G. 3
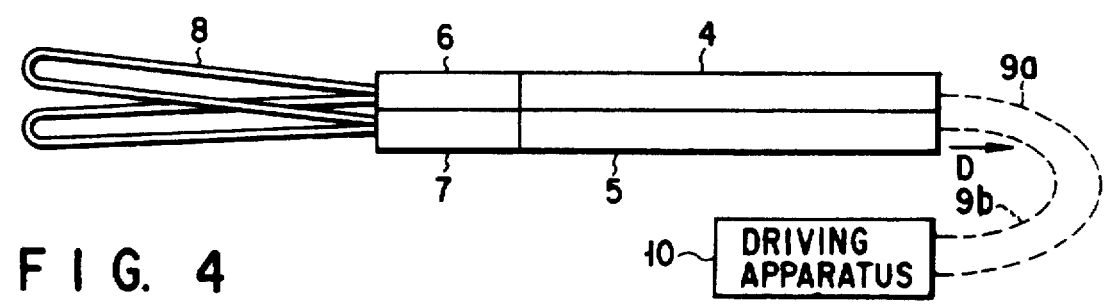
F I G. 4

5,776,047

CARDIOPULMONARY FUNCTION ASSISTING DEVICE

BACKGROUND OF THE INVENTION

1. Field of the Invention

The present invention relates to a cardiopulmonary function assisting device which is to be inserted in a blood vessel, such as the main artery or the main vein to perform part of the pumping function similar to the heartbeat.

2. Description of the Related Art

In general, a balloon pump is used in a case of temporary cardiac incompetence or cardiogenic shock immediately after an open heart surgery. The balloon pump is effective means for decreasing the afterload of the heart and the amount of oxygen consumed by cardiac muscles and increasing the amount of blood flowing through the coronary artery, in order to facilitate a recovery of the functions of the heart. However, the pump executes only part of the pumping function in association with the action of the heart. Therefore, if the gas exchanging function of the lung is lowered along with the lowering of the action of the heart, the pump cannot assist the function of the lung and an additional oxygenator, such as an artificial lung, is required.

If the function of oxygenating venous blood is not fulfilled due to the considerable lowering of the gas exchanging function of the lung, a cardiopulmonary machine may be employed as assistant means to bypass blood from a vein to an artery using an extracorporeal circulator system in which an artificial lung and a blood pump are combined. This system allows powerful circulatory assistance to both the pumping function of the heart and the gas exchanging function of the lung.

Recently, a treatment has been tried, using a device similar in shape and function to an integrated member of blood oxygenating elements of a membrane artificial lung using hollow fibers. The device is directly inserted in the main vein to oxygenate blood.

However, when the above extracorporeal circulatory system is used, since both an artificial lung and a blood pump are required, the apparatus is complex and the handling thereof is complicated.

In the case where the aforementioned device, similar in shape and function to an integrated member of blood oxygenating elements, is used, when the device is left in the blood vessel, it obstructs the blood flow. In this case, a thrombus may be formed where blood stagnates. For this reason, the device has only a limited range of application.

SUMMARY OF THE INVENTION

It is accordingly an object of the present invention to provide a cardiopulmonary function assisting device which not only assists part of the pumping function of the heart but also oxygenates blood, which does not obstruct the blood when left in a blood vessel, so that a thrombus may not easily be formed, and which is accordingly multipurpose, simple in structure and easy to operate.

The cardiopulmonary function assisting device of the present invention comprises: at least one balloon to be left in a blood vessel, the balloon being formed of a gas permeable film; and gas supplying and discharging means, connected to the balloon, for supplying oxygen or a mixture of oxygen and another gas to the balloon so as to expand the balloon and discharging the gas from the balloon so as to contract the balloon, wherein, when the gas is supplied to the balloon, the balloon is expanded, so that oxygen is added through the balloon to blood on a periphery of the balloon and the blood on the periphery of the balloon is removed away by the expansion of the balloon; and when the gas is discharged from the balloon, the periphery of the balloon is filled with blood.

With the cardiopulmonary function assisting device of the present invention, the balloon is repeatedly expanded and contracted, to supply fresh oxygen to blood and assist part of the pumping function of the heart by periodically removing and filling blood, like the heartbeat, from and into a periphery portion of the balloon.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWING

The accompanying drawing, which is incorporated in and constitutes a part of the specification, illustrates presently preferred embodiments of the invention and, together with the general description given above and the detailed description of the preferred embodiments given below, serves to explain the principles of the invention.

FIG. 1 is a side view of a cardiopulmonary function assisting device according to a first embodiment of the present invention, in which balloons are expanded;

FIG. 2 is a side view of a cardiopulmonary function assisting device according to the first embodiment, in which balloons are contracted;

FIG. 3 is a side view of a cardiopulmonary function assisting device according to a second embodiment of the present invention, in which balloons are expanded; and FIG. 4 is a side view of a cardiopulmonary function assisting device according to the second embodiment, in which balloons are contracted.

DETAILED DESCRIPTION OF THE PREFERRED EMBODIMENTS

A cardiopulmonary function assisting device according to a first embodiment of the present invention will be described with reference to the accompanying drawing.

FIGS. 1 and 2 show a cardiopulmonary function assisting device of the first embodiment. FIG. 1 shows a state in which balloons are expanded and FIG. 2 shows a state in which balloons are contracted.

In these figures, a reference numeral 1 denotes a cylindrical gas guide tube, both ends of which are opened. The proximal end of the gas guide tube 1 is connected through a flexible tube 9 to a driving apparatus (e.g., an intra-aortic balloon pump system or a gas loaded artificial heart driving device) 10. The driving apparatus 10, provided outside the human body, supplies and draws gas (oxygen or an oxygen-containing gas) to and from the gas guide tube 1. The distal end of the gas guide tube 1 is coaxially attached to and communicates with a header 2 constituted by a cylindrical body having the same diameters (inner and outer diameters) as those of the gas guide tube 1. Each of the gas guide tube 1 and the header 2 is formed of a material, which does not transmit gas or liquid such as blood and has a suitable rigidity and flexibility, for example, a polymeric material, such as polyvinyl chloride, polyurethane, or silicone resin. The dimensions of the gas guide tube 1 and the header 2 can be set to desired values. For example, the sum of the lengths of the tube 1 and the header 2 can be set to 50 to 150 cm, and the outer diameter and the thickness of each of the tube 1 and the header 2 can be set to 3 to 20 mm and 0.2 to 1.0 mm, respectively.

A plurality of (three in this embodiment) intravascular oxygenating balloons 3 are attached to the header 2. Each of the balloons 3 is shaped like an elongated elliptic bulb, when it is expanded. The proximal end of each balloon 3 is attached to a portion of an open end of the header 2. The other portions of the open end of the header 2, to which the balloons are not attached, are sealed, so that gas introduced to the header 2 through the gas guide tube 1 can effectively enter the balloons and expand them, without leaking. The header 2 is constructed so that the gas supplied therethrough can be distributed equally to the balloons. For example, the plurality of balloons 3 are attached to the header 2 at regular intervals, or the header 2 has flow paths of the same number as that of the balloons 3, which are respectively coupled with the balloons 3. Therefore, if a plurality of balloons are attached to the gas introducing tube 1 so that gas can be equally distributed to the balloons or a single balloon is used, the header 2 can be omitted. In a case where a single balloon is used, it is preferable that the surface of the balloon be plaited or rugged to increase the surface area.

To connect the balloon 3 to the header 2 or the gas guide tube 1, welding, adhesion, caulking or fusing can be employed depending on the materials to be connected. In any case, it is important that gas and blood do not leak from a connected portion.

The balloon 3 may be formed of a gas permeable homogeneous film, for example, a polymeric film such as silicone rubber. The dimensions of the balloon vary depending on the position at which it is used. For example, the length can be 5 to 50 cm, the thickness can be 0.05 to 0.3 mm, and the diameter of the set of balloons in an expanded state can be substantially the same as the inner diameter of a blood vessel, i.e., 10 mm to 35 mm.

It is preferable that the gas (oxygen) permeability of the balloon 3 be as high as possible, since the higher the permeability, the lower the resistance of gas exchanged with blood. When the balloon 3 is expanded and contracted, the pressures of the gas (oxygen or an oxygen-containing gas) in an expanded state and in a contracted state should preferably be controlled to, as in the conventional balloon pump in the main artery, so that the film can be folded in the contracted state, and the film itself is little stretched or contracted, elastically. The pressures of the gas in the expanded and contracted states are respectively controlled to, for example, a positive pressure of about 20 to 400 mmHg (gauge pressure) and a negative pressure of about −20 to −400 mmHg (gauge pressure).

An operation of the cardiopulmonary function assisting device having the aforementioned structure will now be described.

The balloons 3 are left in a blood vessel such as the main artery or the main vein and the gas guide tube 1 is passed through the blood vessel. The proximal end of the gas guide tube 1 is led outside the body and connected to the driving apparatus 10. An oxygen-concentrated gas (e.g., pure oxygen or a mixture of oxygen and air) is supplied from the driving apparatus into the gas guide tube 1 in the direction indicated by the arrow A in FIG. 1 (it is preferable that the oxygen concentration be 21% to 100%, depending on the conditions of the patient). As a result, the gas is introduced to the respective balloons 3 through the header 2, so that the balloons 2 are expanded as shown in FIG. 1. When or after the balloons are expanded, oxygen in the gas is diffused through the balloons 3 into blood. As a result, the blood surrounding the balloons is oxygenated, and at the same time, removed away by the expanded balloons. Subsequently, the oxygen-concentrated gas is drawn from the gas guide tube 1 as indicated by the arrow B in FIG. 2, thereby contracting the balloons 3. As a result, the balloons are contracted and the outer periphery thereof is filled with the blood. The gas is thus repeatedly introduced into and drawn from the gas guide tube 1, thereby supplying fresh oxygen to the blood, and removing and filling the blood surrounding the balloons periodically and repeatedly, like the heartbeat, so as to assist part of the pumping function of the heart. Since the balloons are alternately expanded and contracted, the flow resistance of the blood can be relatively small as compared to the case in which the balloons are always expanded. For this reason, the blood stagnation is less, so that the possibility of formation of a thrombus is reduced, thereby increasing the range of application. Moreover, as described above, the structure is simple and the operability is satisfactory.

A cardiopulmonary function assisting device according to another embodiment will be described with reference to FIGS. 3 and 4.

FIG. 3 shows a state in which balloons are expanded and FIG. 4 shows a state in which balloons are contracted.

In these drawings, a reference numeral 4 denotes a gas inlet tube, both ends of which are opened, and a reference numeral 5 denotes a gas outlet tube, arranged alongside the gas inlet tube 4. The gas outlet tube 5 has the same shape and dimensions as those of the gas inlet tube 4. The distal ends of the gas inlet and outlet tubes 4 and 5 are respectively connected to an inlet and outlet side headers 6 and 7. The distal ends of the inlet and outlet side headers 6 and 7 are connected to a plurality of (two in this embodiment) tubular balloons 8. Each balloon 8 is shaped like an elongated tube, both ends of which are opened. One end of each balloon is connected to an open end of the inlet side header 6 and the other end is connected to an open end of the outlet side header 7, so that the balloon can communicate with the headers.

The dimensions and the materials of gas inlet and outlet tubes 4 and 5, and the inlet and outlet side headers 6 and 7 are similar to those of the gas guide tube 1 and the header 2 of the first embodiment. The dimensions and the material of the balloon 8 are similar to those of the balloon 3 of the first embodiment.

An operation of the cardiopulmonary function assisting device having the aforementioned structure will now be described.

The tubular balloons 8 are left in a blood vessel such as the main artery or the main vein, and the gas inlet tube 4 and the gas outlet tube 5 integral thereto are passed through the blood vessel to the outside of the body. The proximal end of the gas inlet tube 4 is connected to a gas supplying apparatus through a flexible tube 9a and the proximal end of the gas outlet tube 5 is connected to a gas drawing apparatus through a flexible tube 9b (actually, the gas supplying apparatus and the gas drawing apparatus are constituted as one unit, a driving apparatus 10). An oxygen-concentrated gas (e.g., pure oxygen or a mixture of oxygen and air) is supplied from the driving apparatus into the gas inlet tube 4 in the direction indicated by the arrow C in FIG. 3. As a result, the gas is introduced to the respective balloons 8 through the inlet side header 6, so that the balloons 8 are expanded as shown in FIG. 3. When or after the balloons are expanded, oxygen in the gas is diffused through the balloons into blood. As a result, the blood surrounding the balloons is oxygenated, and at the same time, removed away by the expanded balloons. Subsequently, the gas supply to the gas inlet tube 4 is stopped and the gas in the balloons 8 is drawn through the gas outlet tube 5 in the direction indicated by the arrow D in FIG. 4, thereby contracting the balloons 8. As a result, the balloons are contracted and the periphery thereof is filled with the blood. The gas is thus repeatedly introduced into and drawn from the balloons 8, thereby supplying fresh oxygen to the blood, and removing and filling the blood surrounding the balloons periodically and repeatedly, like the heartbeat, so as to assist part of the pumping function of the heart. Since the balloons are alternately expanded and contracted, the flow resistance of the blood can be relatively small as compared to the case in which the balloons are always expanded. For this reason, the blood stagnation is less, so that the possibility of formation of a thrombus is reduced, thereby increasing the range of application. Moreover, as described above, the structure is simple and the operability is satisfactory. The cardiopulmonary function assisting device of this embodiment is disadvantageous in that the diameter of the tubes is greater than that of the first embodiment, since the gas inlet and outlet tubes 4 and 5 are arranged alongside. However, it is advantageous in that fresh oxygen-concentrated gas can always be supplied to the balloons, since the oxygen-concentrated gas flows in only one direction.

In the above embodiments, the balloons are shaped like an elongated elliptic bulb and a linear tube, respectively. However, the balloons are not limited to these shapes. For example, in the first embodiment, the balloons may be shaped like the head of a painting brush, which is tapered toward the tip. In the second embodiment, the balloons may be shaped like an elongated elliptic bulb as in the first embodiment. Thus, the shape of the balloons can be variously modified in accordance with the position or the object of use. The other members of the device can also be modified in accordance with the object of use.

As has been described above, the cardiopulmonary function assisting device of the present invention not only assists part of the pumping function of the heart but also oxygenates blood, and does not obstruct blood when the device is left in a blood vessel, so that a thrombus may not easily be formed. Accordingly, the device is multipurpose, simple in structure and easy to operate.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A cardiopulmonary function assisting device comprising:
   a plurality of balloons arranged side by side to be left in a blood vessel, the balloons being formed of a gas permeable film; and
   gas supplying and discharging means, connected to the balloons, for supplying oxygen or a mixture of oxygen and another gas to the balloons so as to simultaneously expand the balloons and discharging the gas from the balloons so as to simultaneously contract the balloons,
   wherein, when the gas is supplied to the balloons, the balloons are expanded, so that oxygen is added through the balloons to blood on peripheries of the balloons and the blood on the peripheries of the balloons is removed away by the balloons; and when the gas is discharged from the balloons; the peripheries of the balloons are filled with blood.

2. The cardiopulmonary function assisting device, according to claim 1, wherein the gas supplying and discharging means includes a cylindrical gas guide tube having one end connected to said balloons.

3. The cardiopulmonary function assisting device, according to claim 2, wherein the gas guide tube is formed of a polymeric material.

4. The cardiopulmonary function assisting device, according to any one of claims 1 to 3, wherein said balloons are formed of a polymeric film.

5. The cardiopulmonary function assisting device according to claim 1, wherein the balloons are formed of films of a material having little contraction and stretching properties, and the films are folded when the balloons are contracted.

6. The cardiopulmonary function assisting device according to claim 1, wherein the balloons when expanded have an outer diameter substantially the same as an inner diameter of the blood vessel in which the balloons are inserted.

7. The cardiopulmonary function assisting device according to claim 1, wherein the gas supplying and discharging means includes a gas inlet tube having one end connected to said balloons and a gas outlet tube arranged alongside the gas inlet tube and having one end connected to said balloons.

* * * * *